United States Patent [19]

Jackson

[11] Patent Number: 5,747,523
[45] Date of Patent: May 5, 1998

[54] SUBSTITUTED ETHYL α,α-DIARYLMETHYL ETHER DERIVATIVES

[75] Inventor: Paul F. Jackson, Bel Air, Md.

[73] Assignee: Guilford Pharmaceuticals Inc., Baltimore, Md.

[21] Appl. No.: 590,641

[22] Filed: Jan. 24, 1996

[51] Int. Cl.$^6$ .......... A01N 43/36; C07D 207/30; C07D 207/18; C07D 207/04
[52] U.S. Cl. .......... 514/427; 514/428; 548/562; 548/565; 548/574
[58] Field of Search .......... 548/562, 565, 548/574; 514/427, 428

[56] References Cited

U.S. PATENT DOCUMENTS

| | | | |
|---|---|---|---|
| 2,454,092 | 11/1948 | Rieveschl, Jr. et al. | 260/243 |
| 3,658,813 | 4/1972 | Godefroi et al. | 260/240 |
| 4,278,800 | 7/1981 | Rentzea et al. | 548/262 |
| 4,584,384 | 4/1986 | Roantree et al. | 546/281 |
| 4,636,518 | 1/1987 | Fellner et al. | 514/397 |
| 4,657,923 | 4/1987 | Di Schiena | 514/399 |
| 4,762,843 | 8/1988 | Caprathe et al. | 514/293 |
| 4,957,927 | 9/1990 | Ferrand et al. | 514/428 |
| 4,999,361 | 3/1991 | Tsaklakidis et al. | 514/333 |
| 5,039,802 | 8/1991 | Blacklock et al. | 546/165 |
| 5,071,859 | 12/1991 | Knudsen et al. | 514/326 |
| 5,130,309 | 7/1992 | Shanklin, Jr. et al. | 514/210 |
| 5,134,154 | 7/1992 | Freedman et al. | 514/401 |
| 5,180,729 | 1/1993 | Cook | 514/317 |
| 5,262,428 | 11/1993 | Davies et al. | 514/304 |
| 5,268,480 | 12/1993 | Kozilowski | 546/23 |
| 5,298,509 | 3/1994 | Schuster et al. | 514/284 |
| 5,461,068 | 10/1995 | Thaler et al. | 514/399 |

FOREIGN PATENT DOCUMENTS

| | | |
|---|---|---|
| 4341605A1 | 8/1995 | Germany. |
| 685523 | 8/1948 | United Kingdom. |

OTHER PUBLICATIONS

Guido et. al., "Qualitative Organic . . . TLC Data", Chem. Abstract, vol. 121 (1994), pp. 244897.

Primary Examiner—Mukund J. Shah
Assistant Examiner—Tamthom T. Ngo
Attorney, Agent, or Firm—Nath & Associates; Gary M. Nath; Suet M. Chong

[57] ABSTRACT

The invention relates to substituted ethyl α,α-diarylmethyl ether derivatives and pharmaceutically acceptable salts thereof, pharmaceutical compositions comprising the same, and methods of treating cocaine addiction and overdose, and diseases and conditions characterized by abnormal dopaminergic neurotransmission, using the same.

21 Claims, No Drawings

SUBSTITUTED ETHYL α,α-DIARYLMETHYL ETHER DERIVATIVES

BACKGROUND OF THE INVENTION

Dopamine is a catecholamine which is one of the principal neurotransmitters present in the central nervous system. Abnormalities in dopaminergic neurotransmission have been implicated in a variety of disease states including Parkinson's disease, depression, attention deficit disorder, and drug addiction.

The major pathway by which monoamines are inactivated is by being transported back into the cell that released them via specific transporter proteins (i.e. serotonin, norepinephrine, and dopamine transporter proteins). The dopamine transporter protein is the carrier molecule which transports dopamine across the synaptic membrane (Hitri et al., Clinical Neuropharmacology, 1994, 17, 1–22). The human dopamine transporter protein was recently cloned, and shown to have several binding sites, including a binding site for cocaine (Giros et al., Mol. Pharmacol., 1992, 42, 383–390).

Major depression, which is characterized by feelings of intense sadness or pessimistic worry, affects approximately 5–10% of the population (Michels, (ed.) Psychiatry Philadelphia: Lipincott, 1992). A variety of medications have shown efficacy in treating depression including the tricyclic antidepressants, serotonin uptake inhibitors, and monoamine oxidase inhibitors (Pinder et al., Med. Res. Rev., 1993, 13, 259–325). All of these compounds work by increasing the synaptic levels of monoamine neurotransmitters. There are several reports in the literature of selective dopamine uptake inhibitors showing efficacy in animal models of depression (Nielsen et al., Adv. Biosci., 1990, 77, 101–108; Randrup et al., Psychopharmacology, 1977, 52, 73–77; Halaris et al., Biochem. Pharmacol., 1975, 24, 1896–1897).

Parkinson's disease is a progressive, degenerative neurologic motor disorder produced by the loss of dopaminergic neurons in the substantia nigra. This in turn results in abnormally low levels of dopamine present in the striatum. As a result, drugs that can increase the levels of dopamine have the potential to be useful in the treatment of Parkinson's Disease. The most widely prescribed drug in this class is the dopamine precursor levodopa (L-DOPA) (McDowell et al., Ann. Intern. Med., 1970, 72, 29–35). Another mechanism to increase levels of synaptic dopamine is to block its reuptake via inhibition of the dopamine transporter protein. There have been several studies demonstrating that compounds which act by inhibiting the action of the dopamine transporter protein are effective in animal models of Parkinson's Disease (Mayer et al., MPTP: Neurotoxin Prod. Parkinsonian Syndr., Markey et al., ed., 1985, 585–589). For example, the selective dopamine uptake inhibitor GBR 13,098 is effective at preventing MPTP induced toxicity in mice (Pileblad et al., Neuropharmacology, 1985, 24, 689–692).

Attention deficit disorder (ADD) manifests itself primarily in children. The symptoms include an inability to remain focused on a particular task for an extended period of time (Funk et al., Pediatrics, 1993, 91, 816–819). A variety of drugs have been prescribed for this disease, including dextroamphetamine and methylphenidate. Methylphenidate appears to exert its effects by inhibiting the dopamine transporter, more specifically by binding to the cocaine site on the dopamine transporter (Volkow et al., Arch. Gen. Psychiatry, 1995, 52, 456–63). As a result, compounds which have a similar mode of action at this binding site may also show efficacy in this disease.

Cocaine addiction affects approximately 2.1 million people in the United States (Committee to Study Medication Development and Research at the National Institute on Drug Abuse, "Extent of Illicit Drug Use", Development of Medications for the Treatment of Opiate and Cocaine Additions: Issues for the Government and Private Sector, Fulco, Liverman, Earley, Eds., National Academy Press, Washington, D.C., 1995, 36–37). In the last decade the molecular site of cocaine's addictive properties has been determined to be the dopamine transporter protein (Kuhar et al., TIPS, 1991, 14, 299–302). It was originally proposed that cocaine was a competitive inhibitor of dopamine uptake, coincident with cocaine and dopamine having common binding domains on the transporter protein. However, recent evidence suggest that dopamine and cocaine binding sites on the DAT are distinct (Kityama et al., Proc. Natl. Acad. Sci. USA, 1992, 89, 7782–7785).

Partial agonists and/or antagonists at the cocaine site on the dopamine transporter protein may show efficacy in treating cocaine addiction. Importantly, several compounds which bind to the cocaine binding site have been shown to block the effects of cocaine in vivo. For example, GBR 12909 has been shown to attenuate cocaine-induced activation of mesolimbic dopamine neurons in rat (Baumann et al., J. Pharm. Exp. Therap., 1994, 271, 1216–1222). Compounds which bind to the cocaine site but do not inhibit dopamine uptake (i.e. a cocaine antagonist) may have utility in the treatment of cocaine addiction (Carroll, FI et al., Pharmaceutical News, 1994, 1, 11–17).

There are currently no medications which effectively treat cocaine addiction. Accordingly, a need exists for compounds having an affinity for the cocaine site on a dopamine transporter protein (DAT), without inhibiting dopamine uptake, to aid in the treatment of cocaine addiction.

A further need exists for compounds which inhibit dopamine uptake to aid in the treatment of neurological disorders characterized by abnormal dopaminergic neurotransmission, notably Parkinson's disease, depression, and attention deficit disorder (ADD).

The applicant has discovered new compounds that are useful for the above described treatments.

SUMMARY OF THE INVENTION

The present invention relates to a compound of the formula

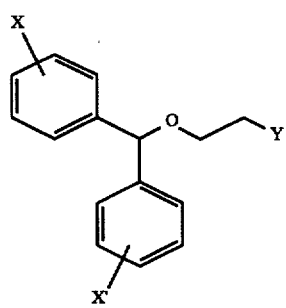

I and pharmaceutically salts thereof, wherein

X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy; and Y is a substituted or unsubstituted, saturated or unsaturated, aliphatic or aromatic heterocyclic amine radical.

The present invention also relates to a pharmaceutical composition comprising:

(a) a therapeutically effective amount of a compound of the formula

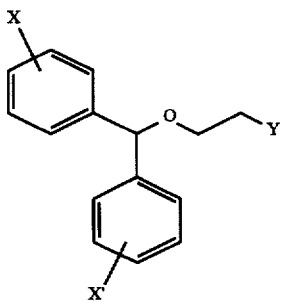

I or a pharmaceutically acceptable salt thereof, wherein

X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy; and Y is a substituted or unsubstituted, saturated or unsaturated, aliphatic or aromatic heterocyclic amine radical; and (b) at least one of a pharmaceutically acceptable carrier, excipient or diluent.

The present invention further relates to a method of treating a disease state or condition characterized by abnormal dopaminergic neurotransmission, which comprises administering to a host suffering therefrom a therapeutically effective amount of a compound having the formula

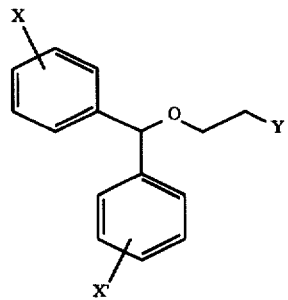

I or a pharmaceutically acceptable salt thereof, wherein

X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy; and Y is a substituted or unsubstituted, saturated or unsaturated, aliphatic or aromatic heterocyclic amine radical.

The present invention also relates to a method of treating cocaine addiction or overdose, which comprises administering to a host suffering therefrom a therapeutically effective amount of a compound having the formula

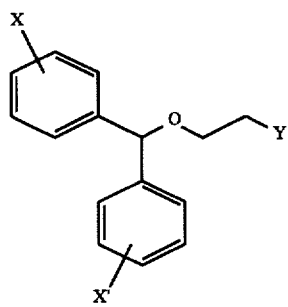

I or a pharmaceutically acceptable salt thereof, wherein

X and X' are independently selected from the group consisting of one or more hydrogen, halo, $C_1$–C6 alkyl, $C_1$–$C_6$ alkenyl, $C_1$–$C_6$ alkynyl, aryl, hydroxy, and alkoxy; and Y is a substituted or unsubstituted, saturated or unsaturated, aliphatic or aromatic heterocyclic amine radical.

DETAILED DESCRIPTION OF THE INVENTION

Definitions

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Alkoxy" means the group —OR wherein R is alkyl as herein defined. Preferably, R is a branched or unbranched saturated hydrocarbon chain containing 1 to 3 carbon atoms.

"Aryl" means an aromatic ring compound such as benzene, phenyl, napthyl and substituted forms thereof.

"Alkenyl" means a straight or branched unsaturated aliphatic hydrocarbon radical having one or more carbon-to-carbon double bonds and from three to six carbon atoms, such as allyl, 2-butenyl, 3-methyl-3-butenyl and the like.

"Alkynyl" means a straight or branched unsaturated hydrocarbon radical having one or more carbon-to-carbon triple bonds and from three to six carbon atoms, such as ethynyl, propynyl, and 1-butynyl.

"Halo" means fluoro, chloro, bromo, or iodo, unless otherwise indicated.

The term "pharmaceutically acceptable salt" refers to salts of the subject compounds which posses the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The term "treatment" as used herein covers any treatment of a disease and/or condition in a mammal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

The system used in naming the intermediates and product compounds of the present invention is as follows. A compound of formula (I) wherein X and X' are fluorine, and Y is pyrrolidine, is named 1-[2-[Bis(4-fluorophenyl)methoxy]ethyl]pyrrolidine.

As used in this specification and the appended claims, the singular forms "a", "an" and "the" include plural references unless the context clearly dictates otherwise. Thus, for example, the reference to a substituted ethyl α,α-diarylmethyl ether derivative includes mixtures of such compounds and so forth.

Compounds of the Invention

The present invention relates to a compound of the formula

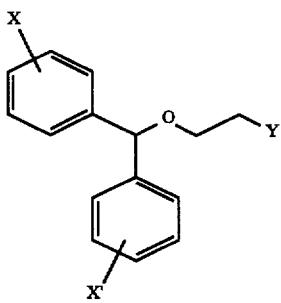

and pharmaceutically salts thereof, wherein

X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy; and Y is a substituted or unsubstituted, saturated or unsaturated, aliphatic or aromatic heterocyclic amine radical.

In a preferred embodiment, X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy. In another preferred embodiment, X and X' are at the para position. In a further preferred embodiment, Y is selected from the group consisting of substituted and unsubstituted azetidine, pyrrolidine, pyrroline, pyrrole, piperidine, pyridine, imidazole and pyrimidine radicals. In another preferred embodiment, Y is a substituted heterocyclic amine, with one or more substituents selected from the group consisting of $C_1$–$C_6$ alkyl, carbonyl, keto, ester, cyclohexyl, cyclohexadienyl, and aryl.

The present invention also relates to a compound of the formula

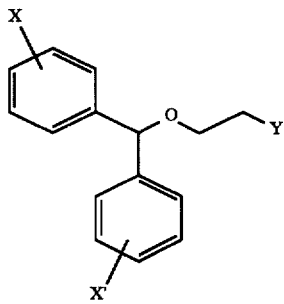

and pharmaceutically salts thereof, wherein

X and X' are independently selected from the group consisting of hydrogen, halo, $C_1$–$C_6$ alkyl, $C_1$–$C_6$ alkenyl, $C_1$–$C_6$ alkynyl, aryl, hydroxy, and alkoxy;

X and X' are at the para position; and

Y is selected from the group consisting of substituted and unsubstituted azetidine, pyrrolidine, pyrroline, pyrrole, piperidine, pyridine, imidazole and pyrimidine radicals.

In a preferred embodiment, Y is a substituted heterocyclic amine radical, with one or more substituents selected from the group consisting of $C_1$–$C_6$ alkyl, carbonyl, keto, ester, cyclohexyl, cyclohexadienyl, and aryl.

Preferred compounds of the present invention are:

1-[2-[Bis(4-fluorophenyl)methoxy]ethyl]azetidine;

1-[2-[Bis(4-fluorophenyl)methoxy]ethyl]pyrrolidine;

1-[2-[Bis(4-fluorophenyl)methoxy]ethyl]-3-pyrroline;

1-[2-[Bis(4-fluorophenyl)methoxy]ethyl]pyrrole;

1-[2-[Bis(4-fluorophenyl)methoxy]ethyl]piperidine.

1-[2-[Bis(4-fluorophenyl)methoxy]ethyl]pyridine;

1-[2-[Bis(4-fluorophenyl)methoxy]ethyl]imidazole; and

1-[2-[Bis(4-fluorophenyl)methoxy]ethyl]pyrimidine.

Methods of Preparation

The compounds of the present invention are prepared according to Scheme I:

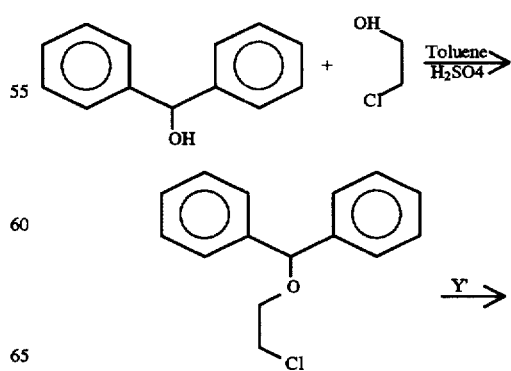

-continued
Scheme I

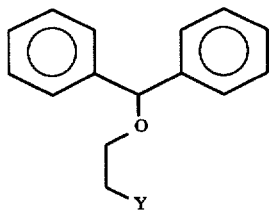

Y' is a heterocyclic amine and Y is the corresponding heterocyclic amine radical.

Substitution of the heterocyclic ring and aryl groups can be achieved by any process known in the art.

EXAMPLES

The following examples are illustrative of the present invention and are not intended to be limitations thereon. All percentages are based on 100% by weight of the final compound.

Example 1

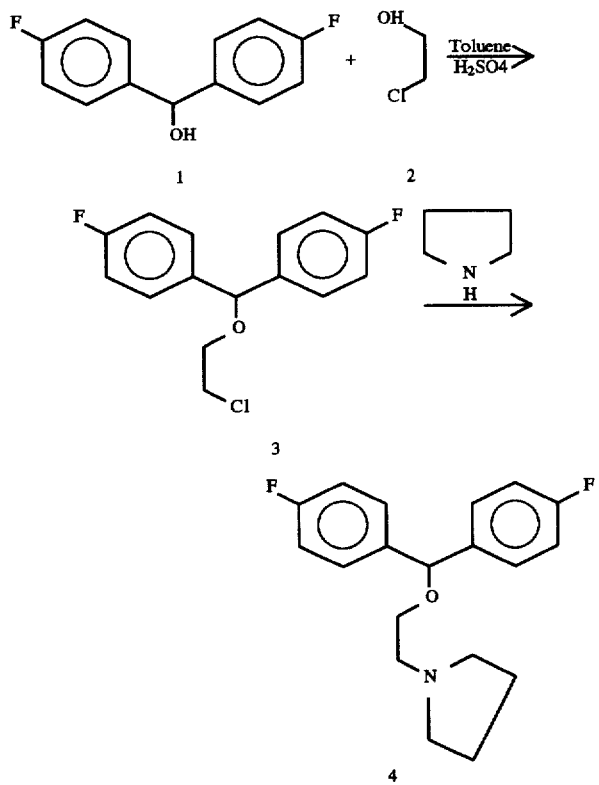

1-[2-[Bis(4-fluorophenyl)methoxy]ethyl]pyrrolidine (4)

1-[Bis(4-fluorophenyl)methoxy]-2-chloroethane (3) (0.92 g, 3.3 mmol) was added to acetonitrile (50 ml) containing potassium carbonate (1.1 g, 8.0 mmol). This was followed by the addition of pyrrolidine (0.51 g, 7.2 mmol). The resulting mixture was then heated to reflux for 72 hours under an atmosphere of nitrogen. At the end of this time, the solution was added to ether (75 ml), washed with water (50 ml) and brine (50 ml). This was then dried over anhydrous magnesium sulfate, filtered and evaporated at reduced pressure to give a clear light yellow oil. The oil was chromatographed on silica gel and eluted with 3:1 ethyl acetate/methanol to afford the desired product (4) (500 mg, 48%) as a clear light yellow oil.

$^1$H NMR (DMSO d$_6$) δ 1.6 (m, 4H), 2.4 (m, 4H), 2.6 (t, 2H), 3.4 (t, 2H), 5.5 (s, 1H), 7.1 (m, 4H), 7.4 (m, 4H)

Example 2

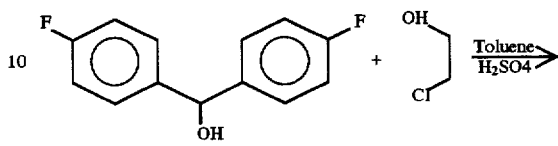

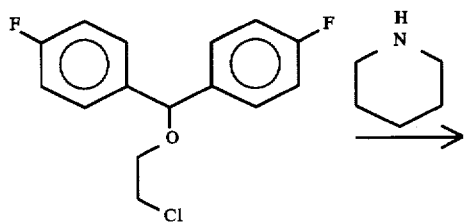

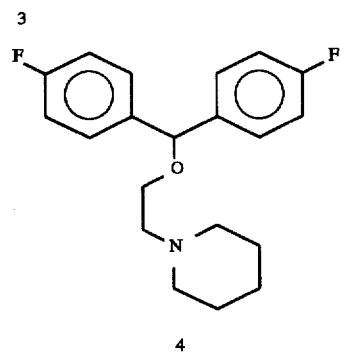

1-[2-[Bis(4-fluorophenyl)methoxy]ethyl]piperidine (5)

1-[Bis(4-fluorophenyl)methoxy]-2-chloroethane (3) (1.03 g, 3.6 mmol) was added to a flask containing acetonitrile (70 ml) and potassium carbonate (1.54 g, 11.1 mmol). This was followed by addition of piperidine (0.69 g, 8.1 mmol). The resulting mixture was heated to reflux for 48 hours under an atmosphere of nitrogen. At the end of this time, the solution was added to ether (75 ml), washed with water (100 ml) followed by brine (100 ml). The solution was then dried over magnesium sulfate, filtered and the solvents were evaporated under reduced pressure. The resulting clear yellow oil was then chromatographed on silica gel and eluted with 3:1 ethyl acetate/methanol to afford the desired product (5) (315 mg, 26.1%) as a clear and colorless oil.

$^1$H NMR (DMSO d$_6$) δ 1.2 (m, 2H) 1.4–1.8 (m, 6H), 2.7 (t, 2H), 3.0 (m, 2H), 3.4 (t, 2H), 5.5 (s, 1H), 7.1 (m, 4H), 7.4 (m, 4H)

Example 3

1-[Bis(4-fluorophenyl)methoxy]-2-chloroethane (3)

2-Chloroethanol (2) (4.1 g, 51 mmol) was added to a 500 ml three neck round bottom flask containing 250 ml of toluene and sulfuric acid(1 ml, 18 mmol). A solution of 4,4'-difluorobenzhydrol (1) (9.16 g, 41.6 mmol) in 50 ml of toluene was then added dropwise over 30 minutes. Once addition was complete the resulting mixture was heated to reflux for 3 hours. At the end of this time the mixture was washed with 10% sodium carbonate (150 ml), water ( 150 ml), and dried over anhydrous magnesium sulfate. The mixture was then filtered and the solvents were evaporated under reduced pressure to afford a clear yellow liquid. The material was distilled on a Kugelrohr distillation apparatus at 140° C., 0.5 mm Hg to afford the desired product (3) (7.0 g, 60%) as a clear and colorless liquid which crystallized slowly upon standing.

$^1$H NMR (DMSO d$_6$) δ 3.63 (t, 2H), 3.80 (t, 2H), 5.6 (s, 1H), 7.18 (DD,4H), 7.4 (dd, 4H)

Pharmacological Activity

Two compounds of formula I were tested in vitro for their ability to displace the cocaine analogue (-)-2-β-[$^3$H] carbomethoxy-3β-(4-fluorophenyl)tropane binding at the cocaine site on the dopamine transporter protein (DAT) (expressed as Ki$_{binding}$), and for their ability to block dopamine uptake into neurons by inhibiting the neuronal dopamine transporter (expressed as Ki$_{uptake}$).

The following Table I compares the Ki$_{binding}$ and Ki$_{uptake}$ values and the uptake to binding ratios (Ki$_{uptake}$/Ki$_{binding}$) of the tested compounds with those of cocaine.

Based on the data in Table I, cocaine is non-selective with an uptake to binding ratio of 1.7. All the tested compounds of formula I exhibit uptake to binding ratios greater than that of cocaine, which mean that the compounds bind potently to the cocaine site on the DAT and have little or no effect on dopamine uptake.

Test Procedures

Values (Ki values) for the binding of compounds at the cocaine binding site of the human dopamine transporter as well as values for the inhibition of dopamine uptake were obtained using methods described in the literature (Kitayama S, Shimada S. Xu H, Markham L, Donovan DM, and Uhl GR. (1992) Proc. Natl. Acad. Sci. USA. 89, 7782–7785), with modifications outlined below. The experimental procedures for the assay of compounds are as follows.

All assays were performed using Chinese Hamster Ovary cells stably expressing the human dopamine transporter cDNA (HDAT cells). hDAT cells were distributed in 96-well

TABLE I

Pharmacological Activity of Compounds of Formula I

| Compound | Affinity to the Cocaine Binding Site (Ki$_{binding}$) | Effect on Dopamine Uptake (Ki$_{uptake}$) | Uptake to Binding Ratio (Ki$_{uptake}$/Ki$_{binding}$) |
|---|---|---|---|
| Cocaine | 0.12 μM | 0.20 μM | 1.67 |
| 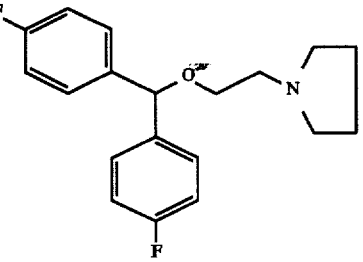 1-[2-[Bis(4-fluorophenyl)methoxy]ethyl]pyrrolidine | 0.361 μM | 0.947 μM | 2.623 |
| 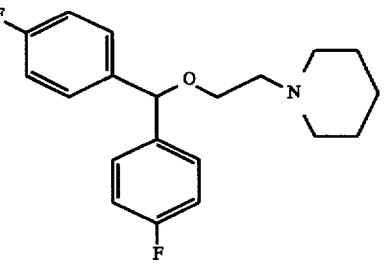 1-[2-[Bis(4-fluorophenyl)methoxy]ethyl]piperidine | 0.211 μM | 0.609 μM | 2.896 |

Ki$_{binding}$, represents the potency of cocaine (a cocaine analogue is used in place of cocaine in the test procedures because cocaine itself is unstable) in binding to the dopamine transporter protein (DAT). Thus, the lower the Ki$_{binding}$ values means the greater the ability of the tested compounds to antagonize cocaine's binding to the DAT.

Ki$_{uptake}$ represents the levels of dopamine uptake. The higher the Ki$_{uptake}$ values means the higher the selectivity of the tested compounds in binding to the cocaine site on the DAT and, thus, the lower the inhibition of the functioning of the DAT.

plates and grown 3 to 4 days to confluency (~10$^5$ cells/well) in Ham's F12 medium containing 10% fetal calf serum. To facilitate comparisons, dopamine uptake and cocaine analogue binding were performed under identical conditions including assay buffers, temperature and time as detailed below.

[$^3$H] DOPAMINE UPTAKE

To assess [$^3$H]dopamine uptake, the hDAT cells were washed two times in Krebs-Ringer-HEPES buffer containing 100 μM ascorbic acid (KRH+) at room temperature. Cells were then incubated with 100 nM [$^3$H]dopamine (24.1 Ci/mmol; NEN) in KRH+ buffer for 6 minutes at room temperature. Co-incubation with 100 μM unlabeled (-)cocaine in parallel incubations allowed estimation of nonspecific uptake. Uptake was terminated by five washes with ice-cold KRH+ and radioactivity was quantitated using a Packard TopLoad Scintillation Counter.

For uptake inhibition studies, cells were pre-incubated with the test compound for 2 hours in cell culture medium at 37° C. Subsequently, the hDAT cells were washed two times in KRH+ buffer at room temperature. The cells were then incubated with 100 nM [$^3$H]dopamine and test compound in KRH+ buffer at room temperature for 6 minutes. Uptake was terminated and quantified as above. Data was analyzed and inhibition constants (Ki) were calculated using the Origin™ computer program by Microcal Software, Inc.

[$^3$H]CFT BINDING

To assess binding of the cocaine analogue (-)-2β[$^3$H] carbomethoxy-3β-(4-fluorophenyl)tropane (CFT), the hDAT cells were washed two times in Krebs-Ringer-HEPES (KRH) buffer at room temperature. Cells were then incubated with 5 nM [$^3$H]CFT (87 Ci/mmol; NEN) in KRH buffer for 6 minutes at room temperature. Co-incubation with 100 μM unlabeled (-)cocaine in parallel incubations allowed estimation of nonspecific binding. Binding was terminated by five washes with ice-cold KRH and radioactivity was quantitated using a Packard TopLoad Scintillation Counter.

For binding inhibition studies, the hDAT cells were pre-incubated with test compound for 2 hours in cell culture medium at 37° C. Subsequently, the cells were washed three times in KRH buffer at room temperature. The cells were then incubated with 5 nM [$^3$H] CFT and test compound in KRH buffer at room temperature for 6 minutes. Binding was terminated and quantified as above. Data was analyzed and inhibition constants ($K_i$) were calculated using the Origin™ computer program by Microcal Software, Inc.

Utility and Administration

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of the present invention can be administered to humans undergoing treatment for cocaine treatment or overdose, or for disease states and conditions characterized by abnormal dopaminergic neurotransmission. The compounds of the present invention can also be administered to mammals other than humans for treatment of various mammalian disease states and conditions characterized by abnormal dopaminergic neurotransmission.

The compounds of the present invention exhibiting uptake to binding ratios greater than that of cocaine, bind potently to the cocaine site on the dopamine transporter protein and have little or no effect on dopamine uptake. This activity is useful in the treatment of cocaine addiction and overdose.

The compounds of the present invention which bind at the cocaine site, but are not completely selective, may inhibit dopamine reuptake. This activity is useful in the treatment of disease states and conditions characterized by abnormal dopaminergic neurotransmission, including without limitation: Parkinson's disease, depression, attention deficit disorder (ADD), hypertension, congestive heart failure, acute and chronic renal failure, angina, hyperprolatenemia, psychoses, galactorrhea, menstrual disorders, sexual dysfunction, Huntington's chorea, schizophrenia and Tourette's syndrome.

For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the drug complex should readily penetrate the blood-brain barrier when peripherally administered. Compounds of this invention which cannot penetrate the blood-brain barrier can be effectively administered by an intraventricular route.

The compounds may be in the form of a sterile injectable preparation, for example as a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets or oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is optimally combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract can be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

Pharmaceutical Compositions of the Invention

The present invention also relates to a pharmaceutical composition comprising:

(a) a therapeutically effective amount of a compound of the formula

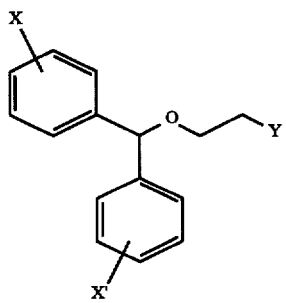

I or a pharmaceutically acceptable salt thereof, wherein

X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy; and Y is a substituted or unsubstituted, saturated or unsaturated, aliphatic or aromatic heterocyclic amine radical; and (b) at least one of a pharmaceutically acceptable carrier, excipient or diluent.

In a preferred embodiment, the compound or the pharmaceutically acceptable salt thereof has an affinity for the cocaine binding site on a dopamine transporter protein (DAT). In another preferred embodiment, the compound or the pharmaceutically acceptable salt thereof permits a dopamine transporter protein (DAT) to maintain its function of accumulating dopamine. More preferably, the compound or the pharmaceutically acceptable salt thereof antagonizes cocaine's binding to a dopamine transporter protein (DAT) while permitting the DAT to maintain its function of accumulating dopamine.

In a further preferred embodiment, the compound or the pharmaceutically acceptable salt thereof has an uptake to binding ratio ($Ki_{uptake}/Ki_{binding}$) greater than that of cocaine. More preferably, the compound or the pharmaceutically acceptable salt thereof has an uptake to binding ratio ($Ki_{uptake}/Ki_{bindig}$) of at least 2.

In a preferred pharmaceutical composition, X and X' are at the para position. In another preferred pharmaceutical composition, Y is selected from the group consisting of substituted and unsubstituted azetidine, pyrrolidine, pyrroline, pyrrole, piperidine, pyridine, imidazole and pyrimidine radicals. In a further preferred composition, Y is a substituted heterocyclic amine radical, with one or more substituents selected from the group consisting of $C_1$–$C_6$ alkyl, carbonyl, keto, ester, cyclohexyl, cyclohexadienyl, and aryl.

The above discussion relating to the utility and administration of the compounds of the present invention is also applicable to the pharmaceutical compositions of the present invention, and thus is hereby incorporated by reference.

Methods of Treating Disease States and Conditions Characterized by Abnormal Dopaminergic Neurotransmission Compounds which bind at the cocaine site and are not completely selective may inhibit dopamine reuptake. Compounds such as these may have utility in treating diseases in which low levels of dopamine have been implicated. The most notable disease states in this class are depression and Parkinson's disease.

Thus, the present invention also relates to a method of treating a disease state or condition characterized by abnormal dopaminergic neurotransmission, which comprises administering to a host suffering therefrom a therapeutically effective amount of a compound having the formula

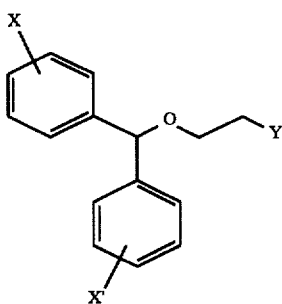

or a pharmaceutically acceptable salt thereof, wherein

X and X' are independently selected from the group consisting of one or more hydrogen, halo, $C_1$–$C_6$, alkyl, $C_1$–$C_6$ alkenyl, $C_1$–$C_6$ alkynyl, aryl, hydroxy, and alkoxy; and Y is a substituted or unsubstituted, saturated or unsaturated, aliphatic or aromatic heterocyclic amine radical.

The treated disease states and conditions include but not limited to Parkinson's disease, depression, attention deficit disorder (ADD), hypertension, congestive heart failure, acute and chronic renal failure, angina, hyperprolatenemia, psychoses, galactorrhea, menstrual disorders, sexual dysfunction, Huntington's chorea, schizophrenia and Tourette's syndrome. Preferably, the treated disease states and conditions are selected from the group consisting of Parkinson's disease, depression, and attention deficit disorder (ADD).

In a preferred method of treatment, X and X' are at the para position. In another preferred method, Y is selected from the group consisting of substituted and unsubstituted azetidine, pyrrolidine, pyrroline, pyrrole, piperidine, pyridine, imidazole and pyrimidine radicals. In a further preferred method, Y is a substituted heterocyclic amine radical, with one or more substituents selected from the group consisting of $C_1$–$C_6$ alkyl, carbonyl, keto, ester, cyclohexyl, cyclohexadienyl, and aryl.

A preferred compound administered for treating a disease state or condition characterized by abnormal dopaminergic neurotransmission, is selected from the group consisting of:

1-[2-[Bis(4-fluorophenyl)methoxy]ethyl]azetidine;

1-[2-[Bis(4-fluorophenyl)methoxy]ethyl]pyrrolidine;

1-[2-[Bis(4-fluorophenyl)methoxy]ethyl]-3pyrroline;

1-[2-[Bis(4-fluorophenyl)methoxy]ethyl]pyrrole;

1-[2-[Bis(4-fluorophenyl)methoxy]ethyl]piperidine.

1-[2-[Bis(4-fluorophenyl)methoxy]ethyl]pyridine;

1-[2-[Bis(4-fluorophenyl)methoxy]ethyl]imidazole; and

1-[2-[Bis(4-fluorophenyl)methoxy]ethyl]pyrimidine.

Methods of Treating Cocaine Addiction and Overdose

Cocaine exerts its reinforcing properties by facilitating the action of the neurotransmitter dopamine in the mesolimbocortical pathways of the brain, a region responsible for the regulation of pleasure and reward. Cocaine does so by inhibiting the functioning of the dopamine transporter (DAT) protein. This inhibition results in excess levels of synaptic dopamine and enhanced dopaminergic transmission.

In 1992, two independent laboratories reported the molecular cloning of the human DAT. Subsequent site-directed mutagenesis studies employing the DAT clone demonstrated that dopamine uptake and cocaine binding occur at distinct sites on the transporter protein. This is significant because it means that drugs can be designed to specifically inhibit cocaine recognition by the DAT while permitting the transporter to maintain its function of accumulating dopamine. This selectivity is important because such a drug would block the physiological effects of cocaine while leaving normal dopamine transmission within the brain intact.

Accordingly, selective cocaine antagonists and mixed agonist/antagonists may have clinical utility in the treatment of cocaine addiction and overdose. Specifically, such compounds would exhibit high uptake to binding ratios ($Ki_{uptake}/Ki_{binding}$), which mean that the compounds would bind potently to the cocaine site on the dopamine transporter protein (expressed as $Ki_{binding}$) and have little or no effect on dopamine uptake (expressed as $Ki_{uptake}$). Stated in other terms, the compounds would antagonize cocaine's binding to the DAT while exhibiting minimal effects on transport function.

Thus, the present invention also relates to a method of treating cocaine addiction or overdose, which comprises administering to a host suffering therefrom a therapeutically effective amount of a compound having the formula

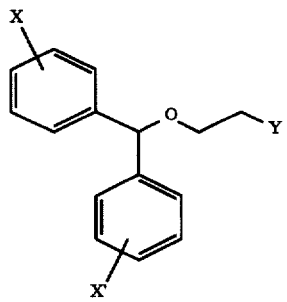

or a pharmaceutically acceptable salt thereof, wherein

X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy; and Y is a substituted or unsubstituted, saturated or unsaturated, aliphatic or aromatic heterocyclic amine radical.

In a preferred embodiment, X and X' are at the para position. In another preferred embodiment, Y is selected from the group consisting of substituted and unsubstituted azetidine, pyrrolidine, pyrroline, pyrrole, piperidine, pyridine, imidazole and pyrimidine radicals. In a further preferred embodiment, Y is a substituted heterocyclic amine radical, with one or more substituents selected from the group consisting of $C_1$–$C_6$ alkyl, carbonyl, keto, ester, cyclohexyl, cyclohexadienyl, and aryl.

A preferred compound administered for treating cocaine addiction or overdose is selected from the group consisting of:

1-[2-[Bis(4-fluorophenyl)methoxy]ethyl]azetidine;

1-[2-[Bis(4-fluorophenyl)methoxy]ethyl]pyrrolidine;

1-[2-[Bis(4-fluorophenyl)methoxy]ethyl]-3-pyrroline;

1-[2-[Bis(4-fluorophenyl)methoxy]ethyl]pyrrole;

1-[2-[Bis(4-fluorophenyl)methoxy]ethyl]piperidine.

1-[2-[Bis(4-fluorophenyl)methoxy]ethyl]pyridine;

1-[2-[Bis(4-fluorophenyl)methoxy]ethyl]imidazole; and

1-[2-[Bis(4-fluorophenyl)methoxy]ethyl]pyrimidine.

All publications and patents identified above are hereby incorporated by reference.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of the formula:

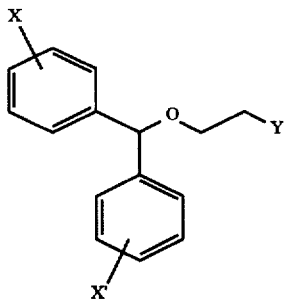

or a pharmaceutically acceptable salt thereof, wherein:

X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy; and Y is a pyrrolidine, pyrroline or pyrrole radical which is unsubstituted or substituted with one or more substituents selected from the group consisting of $C_1$–$C_6$ alkyl, carbonyl, keto, ester, cyclohexyl, and cyclohexadienyl.

2. The compound of claim 1, wherein X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy.

3. The compound of claim 1, wherein X and X' are at the para position.

4. The compound of claim 3, which is selected from the group consisting of:

1-[2-[Bis(4-fluorophenyl)methoxy]ethyl]pyrrolidine;

1-[2-[Bis(4-fluorophenyl)methoxy]ethyl]-3-pyrroline; and

1-[2-[Bis(4-fluorophenyl)methoxy]ethyl]pyrrole.

5. A pharmaceutical composition comprising:

(a) a therapeutically effective amount of a compound of the formula:

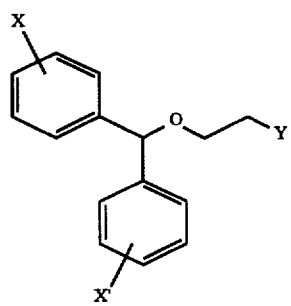

or a pharmaceutically acceptable salt thereof, wherein:

X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy; and Y is a pyrrolidine, pyrroline or pyrrole radical which is unsubstituted or substituted with one or more substituents selected from the group consisting of $C_1$–$C_6$ alkyl, carbonyl, keto, ester, cyclohexyl, and cyclohexadienyl.

(b) at least one of a pharmaceutically acceptable carrier, excipient or diluent.

6. The pharmaceutical composition of claim 5, wherein the compound or the pharmaceutically acceptable salt thereof has an affinity for the cocaine binding site on a dopamine transporter protein (DAT).

7. The pharmaceutical composition of claim 5, wherein the compound or the pharmaceutically acceptable salt thereof permits a dopamine transporter protein (DAT) to maintain its function of accumulating dopamine.

8. The pharmaceutical composition of claim 5, wherein the compound or the pharmaceutically acceptable salt thereof antagonizes cocaine's binding to a dopamine transporter protein (DAT) while permitting the DAT to maintain its function of accumulating dopamine.

9. The pharmaceutical composition of claim 5, which has an uptake to binding ratio ($Ki_{uptake}/Ki_{binding}$) greater than that of cocaine.

10. The pharmaceutical composition of claim 5, which has an uptake to binding ratio ($Ki_{uptake}/Ki_{binding}$) of at least 2.

11. The pharmaceutical composition of claim 5, wherein X and X' are at the para position.

12. The pharmaceutical composition of claim 11, wherein the compound is selected from the group consisting of:

1-[2-[Bis(4-fluorophenyl)methoxy]ethyl]pyrrolidine;

1-[2-[Bis(4-fluorophenyl)methoxy]ethyl]-3-pyrroline; and

1-[2-[Bis(4-fluorophenyl)methoxy]ethyl]pyrrole.

13. A method of treating a disease state or condition characterized by abnormal dopaminergic neurotransmission, which comprises administering to a host suffering therefrom a therapeutically effective amount of a compound having the formula:

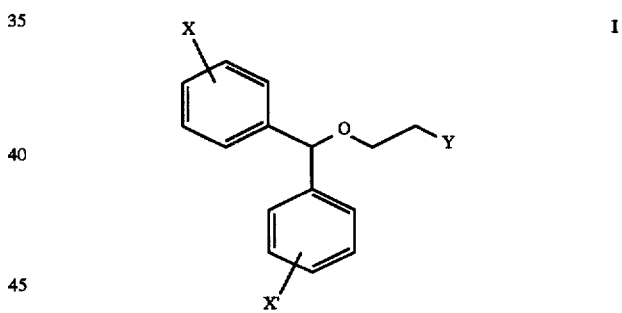

or a pharmaceutically acceptable salt thereof, wherein:

X and X' are independently selected from the group consisting of one or more hydrogen, halo, $C_1$–$C_6$ alkyl, $C_1$–$C_6$ alkenyl, $C_1$–$C_6$ alkynyl, aryl, hydroxy, and alkoxy; and Y is a pyrrolidine, pyrroline or pyrrole radical which is unsubstituted or substituted with one or more substituents selected from the group consisting of $C_1$–$C_6$ alkyl, carbonyl, keto, ester, cyclohexyl, and cyclohexadienyl.

14. The method of claim 13, wherein the disease state or condition is Parkinson's disease.

15. The method of claim 13, wherein the disease state or condition is depression.

16. The method of claim 13, wherein the disease state or condition is attention deficit disorder (ADD).

17. The method of claim 13, wherein X and X' are at the para position.

18. The method of claim 17, wherein the compound is selected from the group consisting of:

1-[2-[Bis(4-fluorophenyl)methoxy]ethyl]pyrrolidine;

1-[2-[Bis(4-fluorophenyl)methoxy]ethyl]-3-pyrroline; and

1-[2-[Bis(4-fluorophenyl)methoxy]ethyl]pyrrole.

19. A method of treating cocaine addiction or overdose, which comprises administering to a host suffering therefrom a therapeutically effective amount of a compound having the formula:

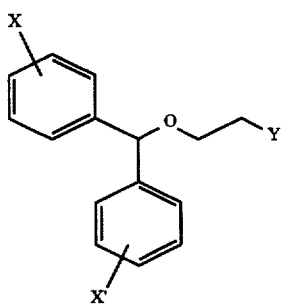

I or a pharmaceutically acceptable salt thereof, wherein:

X and X' are independently selected from the group consisting of one or more hydrogen, halo, $C_1$-$C_6$ alkyl, $C_1$-$C_6$ alkenyl, $C_1$-$C_6$ alkynyl, aryl, hydroxy, and alkoxy; and Y is a pyrrolidine, pyrroline or pyrrole radical which is unsubstituted or substituted with one or more substituents selected from the group consisting of $C_1$-$C_6$ alkyl, carbonyl, keto, ester, cyclohexyl, and cyclohexadienyl.

20. The method of claim 19, wherein X and X' are at the para position.

21. The method of claim 20, wherein the compound is selected from the group consisting of:

1-[2-[Bis(4-fluorophenyl)methoxy]ethyl]pyrrolidine;

1-[2-[Bis(4-fluorophenyl)methoxy]ethyl]-3-pyrroline; and

1-[2-[Bis(4-fluorophenyl)methoxy]ethyl]pyrrole.

* * * * *